(12) United States Patent
Kocher (10) Patent No.: US 11,540,764 B1
(45) Date of Patent: Jan. 3, 2023

(54) GROUP ASSOCIATION SYSTEM AND METHOD BASED ON BRAINWAVE RESPONSE TO EXTERNAL STIMULATION

(71) Applicant: Robert William Kocher, McLean, VA (US)

(72) Inventor: Robert William Kocher, McLean, VA (US)

( * ) Notice: Subject to any disclaimer, the term of this patent is extended or adjusted under 35 U.S.C. 154(b) by 483 days.

(21) Appl. No.: 16/350,403

(22) Filed: Nov. 14, 2018

Related U.S. Application Data (60) Provisional application No. 62/709,333, filed on Jan. 16, 2018.

(51) Int. Cl.
  *A61B 5/378*    (2021.01)
  *A61N 1/05*    (2006.01)
  *A61B 5/00*    (2006.01)
  *A61B 5/291*    (2021.01)

(52) U.S. Cl.
  CPC ............. *A61B 5/378* (2021.01); *A61B 5/291* (2021.01); *A61B 5/6803* (2013.01); *A61N 1/0529* (2013.01); *A61B 5/0006* (2013.01); *A61B 5/4064* (2013.01)

(58) Field of Classification Search
  CPC ....... A61B 5/378; A61B 5/291; A61B 5/6803; A61B 5/0006; A61B 5/4064; A61N 1/0529
  See application file for complete search history.

(56) References Cited

U.S. PATENT DOCUMENTS

2017/0270411 A1* 9/2017 Kocher .................. A61B 5/291

* cited by examiner

*Primary Examiner* — Patrick Fernandes (57) ABSTRACT

A group association system attempts to identify if an individual is "gifted" in any particular area. A group association system is based on brainwave response to stimulation is disclosed. The system including a brainwave stimuli device which provides stimuli to groups of highly skilled, general skilled, and a general population groups, as test stimuli for determination of group association. A brainwave collection device collects brainwaves of individuals, with the brainwave collection device storing collected brainwaves in a brainwave database. A brainwave processing device analyzes brainwaves received from the brainwave database. A brainwave analysis device uses analyst screens, artificial intelligence or machine learning to analyze the brainwaves create at least one signature development module for determination of similar brainwaves related to different individuals' responses to the same stimuli. In addition, at least one signature development module determines which individuals have the same or similar brainwave responses to the same test stimuli.

4 Claims, 7 Drawing Sheets

GROUP ASSOCIATION SYSTEM AND METHOD BASED ON BRAINWAVE RESPONSE TO EXTERNAL STIMULATION

CROSS-REFERENCE TO RELATED APPLICATIONS

This application claims priority from U.S. Provisional Patent Application Ser. No. 62/709,333, filed on Jan. 16, 2018, and titled Group Association System and Method Based on Brainwave Response to External Stimulation. This priority document is incorporated herein by reference, in its entirety.

BACKGROUND

Field of the Invention

The present invention relates to psychophysiological measurement; and more specifically, to techniques for determining group association based on brainwave response to external stimulation.

Description of the Related Art

People are born with different skills sets. There are certain tasks that will be inherently easy for some folks and difficult for others. An individual's brain processes information differently than other individuals. Some people are good at math, art or engineering, while others are not. Good artists do not necessarily make good mechanics. Software engineers are perhaps different than baseball players. Some people are good at thinking in three dimensions; which is a critical ability for astronauts and pilots. There are numerous interests, hobbies, and passions that people have; one question is whether these skills, hobbies and interests are learned or whether it is discovered that a person has a special skill or passion for particular area or field. Sometimes a person is referred as being "gifted" in a particular area.

In 1983, an American developmental psychologist, Howard Gardener, described 9 types of intelligence:
  Naturalist (nature smart)
  Musical (sound smart)
  Logical-mathematical (number/reasoning smart)
  Existential (life smart)
  Interpersonal (people smart)
  Bodily-kinesthetic (body smart)
  Linguistic (word smart)
  Intra-personal (self-smart)
  Spatial (picture smart)

For many decades, determinations relating to aptitude and suitability for different positions have been made through the use of questionnaires and other written types of aptitude testing. As a result, these written tests have been used to determine which candidates are most suitable for a particular job or occupation. A drawback is that some individuals may not be aware which positions would result in them excelling in the job they work in. This can result in many people "washing out" from training, because they are not the most suitable individual for the position they are training for; or perhaps are unable to perform their job well or as well as expected. In colleges across the United States, students generally change majors 2.5 times before graduation. This added cost of education creates a burden for the students and their families and negatively impacts our economy through the cost of repaying education loans. In addition, there is a large cost to the college, military academy, etc. for those on partial or full scholarship, which cannot be recouped, which further impacts our economy in a negative fashion. In addition, some people are not good test takers, or can get nervous while taking standardized tests. As a result, the outcome of the paper tests may skew the test results and millions of dollars are lost through training individuals who are not best suited for the position.

As an example, the cost to produce one F35 pilot beginning with a new person joining the Air Force to becoming a fully qualified fighter pilot is approximately 17 million dollars, in addition to many years of training. There are numerous trainees that washout of the program at a significant cost. The selection process begins with a paper tests then human interviews. This process is similar to the way selection processes were conducted during WWII.

Another interesting situation is that the best qualified or "gifted" persons may not know their skill. They may not have had the opportunity to fly an airplane or attend a good school. For decades, electroencephalography (EEG) and related tools that measure psychophysiological responses (e.g., polygraphs) have been used to discern whether someone is familiar with certain information. Examples of EEG tools include the systems and methods disclosed in U.S. Pat. No. 8,684,926 and U.S. Patent Application Publication 2014/0163409 (each of which is incorporated herein by reference, in its entirety). While EEGs have been used to try to identify knowledge, EEGs have not been used to identify association of groups of individuals who are best suited to be trained for employment in a particular position. While data on psychophysiological responses has been collected in the past, the collected data has not been used in the manner provided by the instant invention.

In summary, paper tests to determine acceptance of an individual are inexact and archaic. Tests, interviews and similar activities which are currently used to determine skill level, are expensive and oftentimes result in making it very difficult to find the right individual to fit a particular job or skillset. The instant invention uses brainwaves, which produce a unique signature when presented with test stimuli, a unique signature that highly skilled "gifted" group (HSG) individuals produce, then testing potential general skilled candidates, and compare their unique brainwave signature to the HSG signature. In response to comparing the brainwave response of individuals of different groups, the best individual candidates should have a high probability of being associated with the unique HSG signature (similar brainwave response to test stimuli). The invention will indicate which group (HSG or non-HSG) a person would be associated with. This will be a game-changer for associating people with groups that have brainwaves which respond similarly to individuals highly successful in the field.

Success can be measured by informing individuals which have unique brainwave responses to test stimuli that compare with HSG they would be associated with, and then allowing them to pursue that skillset and perform at a high level; should they choose to do so. HSG today is comprised of individuals moving through a process via trial and error. Many non-HSG individuals are doing jobs they are neither skilled at nor effective in performing at the position they are in. As noted, above, on average, an individual changes their college major 2.5 times. If they could be tested, they could be advised ahead of time where their skillset would likely be best utilized; as this would be best for all involved and would save a significant amount of time and money.

SUMMARY OF EXEMPLARY EMBODIMENTS OF THE INVENTION

This invention attempts to match a "gifted" person with a particular "gifted" highly skilled group (HSG) by matching brainwave signatures of the tested individual to the best HSG, if one matching brainwave signature exists.

The belief is that a person is born with particular skills, interests, and weaknesses, and that by discovering and individual's skills early, will help an individual into a career path that he or she will enjoy and is destined to do very well in this type of work. A person may be "gifted" in a certain area or areas and not be aware of their unrecognized skill sets.

This invention is a novel approach in determining a person's skills through the process of group association. This approach starts by identifying highly skilled "gifted" group (HSG) then testing through the use of primarily visual stimuli, such as 5,000 photos, and recording the individual's brainwave response. Since we are starting with the HSG 'gifted' group, we are looking for similar responses to similar stimuli. This would lead to a specific HSG signature.

According to an exemplary embodiment, electrodes on a helmet are placed onto the individual's head, and brainwaves are collected. Artificial intelligence then processes the data and produces signatures, with eventual human review of the results. The stimuli consist of high-speed rates of presentation of abstracts, 3D, shapes, ink-based pictures, photographs; which are essentially various forms of non-learned media. Machine learning would look at the signatures produced and draw conclusions. The repeated presentation of stimuli strengthens those conclusions. Also, different facets of EEG would be looked at, and heart rate changes would be measured. In addition, approximately 5000 different stimuli are provided to an individual being tested, and were flashed before the individual at a rate of 4-20 frames per second. In other exemplary embodiments, different types of stimuli may be provided. According to an exemplary embodiment, a group association system based on brainwave response to stimulation is disclosed. The system includes a brainwave stimuli device which provides stimuli to groups of highly skilled, general skilled, and a general population groups, as test stimuli for determination of group association. A brainwave collection device collects brainwaves of individuals, with the brainwave collection device storing collected brainwaves in a brainwave database. A brainwave processing device analyzes brainwaves received from the brainwave database. A brainwave analysis device uses analyst screens or artificial intelligence or machine learning to analyze the brainwaves create at least one signature development module for determination of similar brainwaves related to different individuals' responses to the same stimuli. In addition, at least one signature development module determines which individuals have the same or similar brainwave responses to the same test stimuli. The test stimuli may include 5,000 stimuli at 4-20 frames per second. In the exemplary embodiments disclosed, a sequence of stimuli can be made up of a single stimulus or can be made up of a set of thousands of the same or different types of stimuli. The different test stimuli can be provided by different devices, such as photographs, light, sound and odor.

According to another exemplary embodiment, a group association method based on brainwave response to external stimulation is disclosed. The method including the steps of selecting individuals of a highly skilled group; selecting test stimuli for the individuals of the highly skilled group; exposing the test stimuli to the individuals of the highly skilled group and collecting brainwave responses to each stimuli for each individual in the highly skilled group; analyzing the brainwave responses to the test stimuli by the individuals in the highly skilled group; identifying patterns in the brainwave responses to each test stimuli for each of the individuals in the highly skilled group; and developing one or more signatures in signature development modules for the highly skilled group. Next, selecting individuals of a general skilled group; exposing the test stimuli of the highly skilled group to the general skilled group; analyzing the brainwave responses to the test stimuli of the general skilled group; identifying patterns in the brainwave responses to each test stimuli for each of the individuals in the general skilled group; comparing the brainwave patterns of the general skilled group to the highly skilled group signatures; identifying general skilled group individuals that have highly skilled group signatures; and considering general skilled group individuals for highly skilled group training.

DETAILED DESCRIPTION OF THE EXEMPLARY EMBODIMENTS

Figure 1:
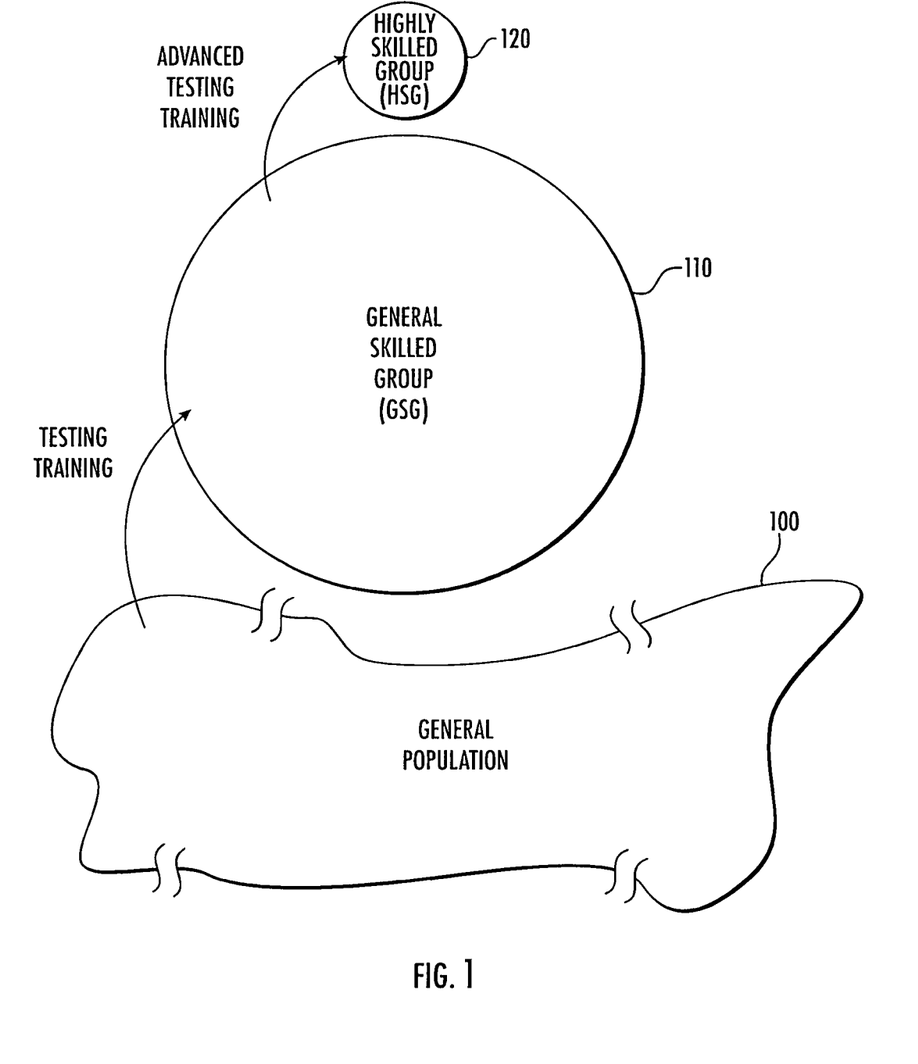
FIG. 1 provides a representation of a plurality of groups of individuals.

FIG. 1 illustrates a representation of three different groups to receive stimuli testing for determination of group association. Group 100 represents the general population who has no specific area of a predetermined area, such as flying helicopters. Group 110 represents a general skilled group who has some training in the area of flying a helicopter, such as helicopter pilots. Group 120 represents individuals in the highly skilled area, such as the top ten pilots in the United States.

Figure 2:
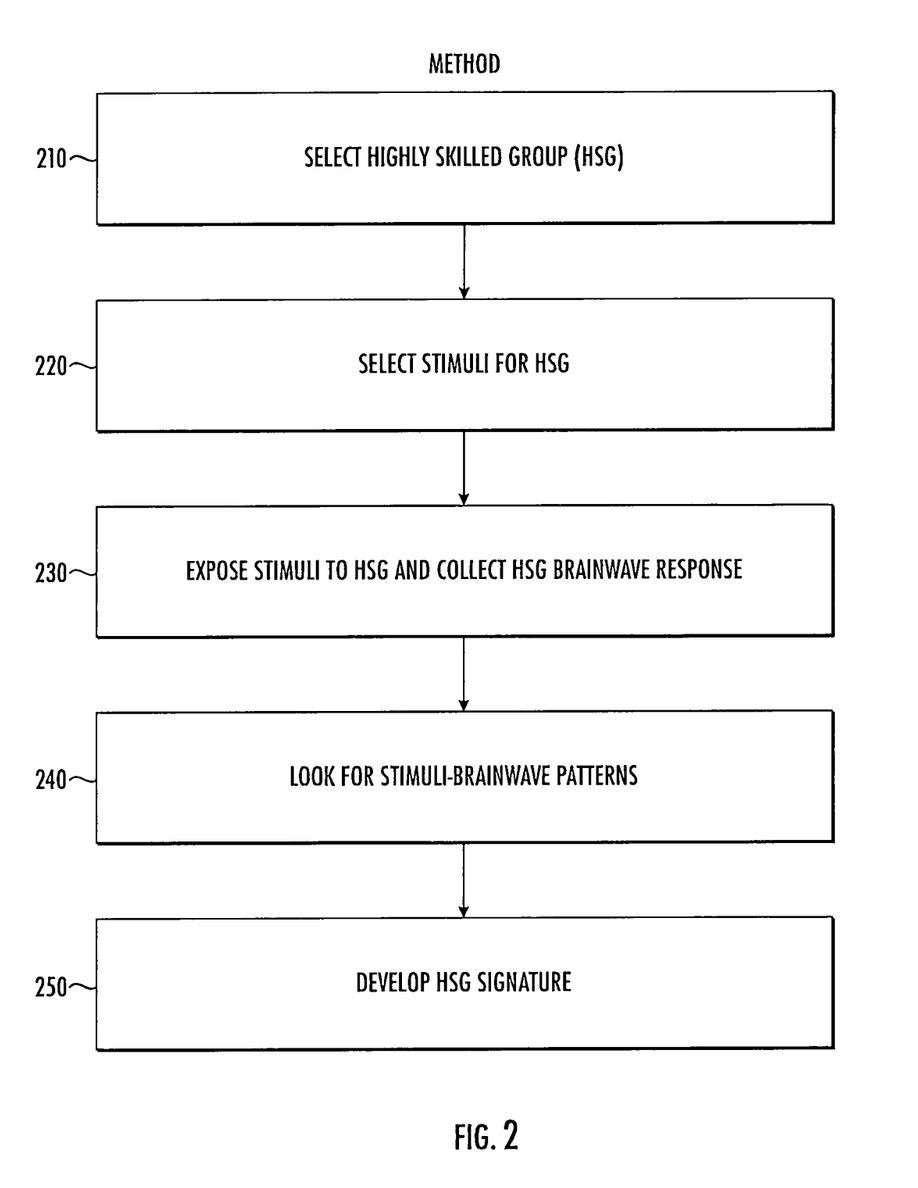
FIG. 2 illustrates a first part of a flowchart representing a group association method based on brainwave response to external stimulation.
Figure 3:
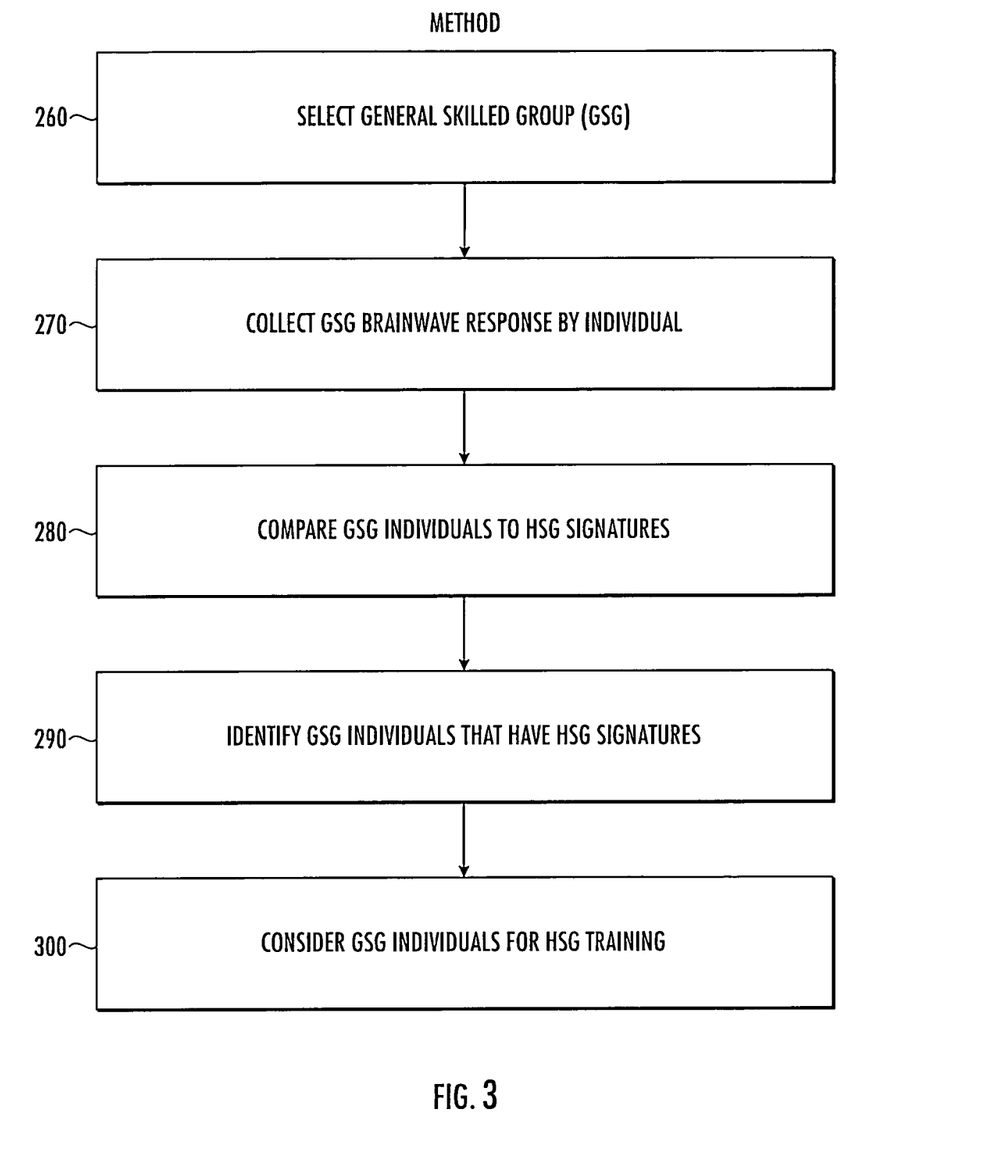
FIG. 3 illustrates a second part of a flowchart representing a group association method based on brainwave response to external stimulation.

FIGS. 2 and 3 represent a method of testing the groups 110 and 120 to identify general skilled pilots to determine who should be recommended to become highly skilled pilots. As shown in step 210, the top members of a highly skilled group are selected. In step 220, test stimuli are selected for testing the members of the highly skilled group, using the same test stimuli for each member of the highly skilled group. The brainwave responses are then collected.

In step 230, the members of the highly skilled group are exposed to the test stimuli and their brainwave responses to each test stimuli are collected and stored in a brainwave database. In step 240, the system looks for patterns in the brainwave responses. In step 250, the system develops brainwave signatures for the highly skilled group individuals. In step 260, members of the general skilled group are selected for testing. In step 270, the members of the general skilled group are exposed to the test stimuli. The brainwave results are then collected, by individual.

In step 280, the brainwaves collected for the general skilled group are compared with the brainwave signatures for the highly skilled group individuals. In step 290, the general skilled individuals that have highly skilled individual's signatures are identified.

In step 300, the general skilled group of individuals is considered for training as highly skilled individuals in the highly skilled individuals group. Although not indicated in the steps, the general population group can be tested with the same test stimuli for consideration of placement into the general skilled group.

Figure 4:
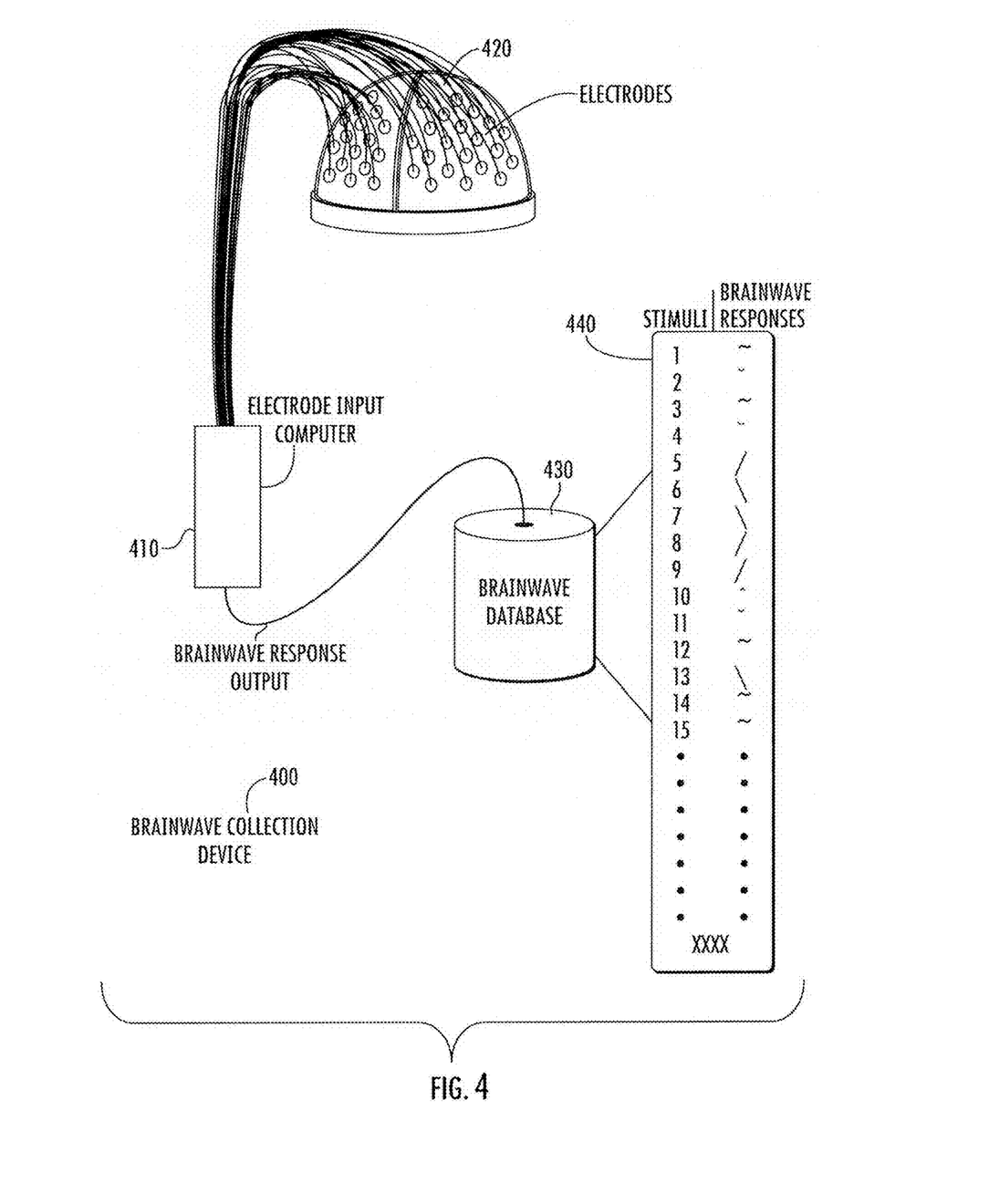
FIG. 4 illustrates a brainwave collection device.

Turning to FIG. 4, Research has established that a test subject's degree of familiarity with external stimuli such as images and sounds, is correlated to strength and timing of brainwave signals observed by electroencephalograms (EEGs). The human brain can absorb and process stimuli at very high rates of presentation. Visual stimuli can be presented rapidly in a technique known as Rapid Serial Visual Presentation. In addition to images, alternative stimuli such as light stimuli, hearing stimuli, touch stimuli, smell stimuli, and taste stimuli may be presented using an analogous rapid serial presentation technique (collectively, the rapid serial presentation of any stimuli are referred to herein as "RSP"). The RSP technique typically displays stimuli to a test subject at rates of 4 to 12 stimuli per second. Depending upon the content and complexity of the information presented and the ability of the test subject to process the information, the presentation rate may be more or less than the typical values.

The brain processes stimuli and produces psychophysiological response to recognition of the stimuli in the form of brainwaves observed by EEG. A response pattern strongly associated with recognition is the "p-300" brainwave which has a characteristic shape observed at about 300 milliseconds (ms) after being exposed to a recognized stimulus. EEG data time-tagged with the display of stimuli presented by the RSP technique enables a subject to be exposed to a large number of stimuli on a particular topic in a relatively short period of time. For instance, assuming a presentation pattern of 3 seconds of display followed by 3 seconds of rest, and a display rate of 8 images per second, a subject could be exposed to 240 images per minute.

EEG can be quantified in various ways by applying a Fourier transformation, including by amplitude, power and frequency, in order to generate numerical values, ratios or percentages; graphically display arrays or trends; and set thresholds. Many quantitative EEG measures can be used to quantify slowing or attenuation of faster frequencies in the EEG. These include the calculation of power within different frequency bands (i.e., delta, theta, alpha and beta); ratios or percentages of power in specific frequency bands; and spectral edge frequencies (based on the frequency under which x % of the EEG resides). These discrete values can then be compared between different regions, such as hemispheres, or between electrode-pair channels. Time-compressed spectral arrays ("Spectrograms") incorporate both power and frequency spectrum data, and can be represented using color to show power at different frequencies. Additional measures include amplitude integrated EEG, which continuously monitors comatose patients by average ranges of peak-to-peak amplitudes displayed using a logarithmic scale, and the commercial Bispectral Index. Other nonparametric methods exist beyond Fourier transformation, including interval or period analysis and alternative transformation techniques. Parametric, mimetic, and spatiotemporal analyses are also available using a variety of computational methods and waveform analysis based on machine learning approaches trained on EEG recordings. Basic measures of total power can be quantified and compared to performance characteristics to identify correlations that can be used to predict the reoccurrence of those performance characteristics.

Brainwave response to recognition also has repeatable and predictable characteristics which can be exploited by digital signal processing algorithms. The brainwave discriminator, often referred to as the classifier component, can be trained in the characteristic nature of the test subject's EEG response when presented with stimulus records or targets known to be familiar to the test subject. The response to such target records provides the classifier component with exemplar characteristics to discriminate records that are not known to be known by the test subject, but probe what the test subject recognizes.

Depending upon the individual test subject and the type of stimuli presented, brainwave indications of recognition in the p-300 may vary in amplitude, character, and latency. A brainwave classifier component algorithm may correlate indications of recognition in brainwaves other than the typical p-300 to strengthen the confidence in recognition or non-recognition.

A test subject may intentionally or unintentionally create circumstances that adversely affect EEG data such that EEG recognition signals are suppressed, masked, or otherwise corrupted. A test-subject that becomes inattentive or intentionally suppresses the senses targeted by the stimuli (e.g., for visual stimuli, averting eyes from display) will not produce responses indicating recognition. Brainwave indications of inattentiveness and external indications of suppressed senses can be used to flag the recognition scoring algorithm to disregard those tests. When the test subject is again attentive to the stimuli, the recognition scores will again be useful indicators of recognition.

Likewise, intentional or unintentional masking of brainwave signals can be accomplished by muscle movements in the face and scalp. EEG signals associated with muscle movement is typically much larger than EEG signals resulting from brain functions. Signals resulting from eye blinks, jaw clinching or scalp motion can be automatically discriminated from brainwave signals and therefore used to adjust recognition scores for target and non-target stimuli.

Presentation of a particular deck may be repeated more than once to strengthen statistical confidence in the EEG indications of recognition or familiarity with particular stimuli. Shuffling the deck (i.e., reordering the target and non-target stimuli) each time it is presented ensures that the brainwave signals observed for target stimuli are due to the content of the stimulus, rather than the presentation order.

The general features of this disclosure provide for an automated system that characterizes brainwave signals from the EEG data to indicate the level of recognition of stimuli, which is presented in multiple sequences of stimuli that are presented to the test subject.

A brainwave response of the subject to stimuli can be detected using sensors. The response may be a p-300 or another brainwave signal. The response can be correlated to at least one target category. A second sequence of stimuli may be selected based upon the brainwave response to one or more stimuli in the first sequence. The second stimuli may be selected automatically or by a user. The first sequence of stimuli can be a baseline sequence.

Proper assembly of the sequence of a deck is a key contributor of the certain embodiments of this disclosure. A test deck may be composed of (i) a small number of target stimuli used to probe the test subject's familiarity on a topic or range of topics, and (ii) a larger number of non-target items unlikely to be recognized by the test subject, but similar in gross characteristics of the target items. For example, the ratio of target to non-target items may range between 1:25 to 1:2.

The size of decks at a particular level of abstraction can be small or large. The deck may be broken into subsets or hands to accommodate the attention span of the test subject or allow more frequent periods of rest between hands.

Target and non-target images in the deck are selected to be similar in physical attributes such as size, color, resolution, and composition. In an exemplary embodiment where the stimuli are sound stimuli, examples may include audio clips, voice, music, and the sounds that relevant things make. Similar to visual presentation decks, sound decks are more diagnostic when target and non-target clips are similar in attributes, such as volume level and background noise levels. This minimizes the occurrence psychophysiological responses that can be more strongly associated with surprise or startle, than with the desired response of recognition.

Optionally, a user may access the sequence of stimuli through the investigator interface and edit the sequence through the editor. The stimuli are then presented to the subject, and the subject's EEG signals are collected, analog processed, converted and digitally processed. Alternatively, the dealer may be located remotely and monitor events through electronic communications.

In another embodiment, an EEG system is disclosed, comprising: sensors, amplifiers, analog filters, AID converters, digital filters, noise rejection components, and signal extraction processing components; a stimulus presentation system capable of reproducing images, video, and sounds, synchronized in time with the sensors, implemented with one or more decks of analog or digital stimulus files which are reproduced serially for reception by human senses and illicit psychophysiological response recorded by the EEG system, wherein the stimulus decks are presented.

In an exemplary embodiment, additional senses may be reproduced and presented to the test subject, including taste, smell and touch; the stimulus deck may be created by hand or by machine. The stimulus deck may be created before presentation or in real-time The system is composed of an EEG subsystem, a stimulus presentation subsystem, a system of stored records of stimuli and an automated data processing subsystem. The EEG subsystem is composed of multiple channels of sensors, amplifiers, analog filters and analog to digital converters. The stimulus presentation subsystem is capable of reproducing multiple records of images, video, or sounds stored in analog or digital files that form decks of stimulus data. The stimulus presentation system is synchronized with the EEG system so that the time of presentation and identity of the stimulus record are associated with the EEG data. Stimulus files in a deck are serially reproduced at a rapid pace for exposure to human senses, which result in a psychophysiological response sensed and recorded by the EEG subsystem. The automated data processing system extracts and characterizes brainwave signals from the EEG data.

All or part of the systems and methods described herein may be implemented as a computer program product that is a non-transitory computer-readable storage medium encoded with computer code that is executable by a processor. All or part of the systems and methods described in this application may be implemented as an apparatus, method, or electronic system that may include one or more processors and storage devices that store executable computer program code to implement the stated functions.

The details of one or more embodiments of the subject matter of this application are set forth in the drawings and descriptions contained in this application. Other features, aspects, and advantages of the subject matter will become apparent from the description, drawings and claims.

The subject matter of this specification functions in a variety of component combinations and contemplates all those types of components a person of ordinary skill in the art would find suitable for functions performed. The figures describe specific components in specific embodiments. However, the range of the types of components mentioned in the description of the figures may be applied to other exemplary embodiments as well.

The terminology used herein is for the purpose of describing particular embodiments only and is not intended to be limiting in any way. As used herein, the singular forms "a," "an," and "the," etc., are intended to include the plural forms as well, unless the context clearly indicates otherwise.

The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The subject matter of this specification is described above with reference to system diagrams, flow diagrams, and screen mockups of systems, methods, and computer program products. Each block or combinations of blocks in the diagrams can be implemented by computer program code and may represent a module, segment, or portion of code. Program code may be written in any combination of one or more programming languages, including object oriented programming languages such as the JAVA®, SMALLTALK®, C++, C#, OBJECTIVEC® programming languages and conventional procedural programming languages, such as the "C" programming language.

It should be noted that, in some alternative exemplary embodiments, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block or combination of blocks in the diagrams can be implemented by special purpose hardware-based systems that perform the specified functions or acts.

Computer program code may be provided to a processor or multiple processors of a computer to produce a particular machine, such that the program code, which executes via the processor, implements the functions specified in the system diagrams, flow diagrams and screen mockups.

The subject matter of this specification may be implemented on one or more physical machines. Each physical machine may be a computer comprising one or more processors and one or more storage devices; however a single processor and a single storage device are sufficient. A person of ordinary skill in the art will recognize the variety of types of computers suitable for the functions described, including desktops, laptops, handset devices, smartphones, tablets, servers, or accessories incorporating computers such as watches, glasses, or wearable computerized shoes or textiles. A non-exhaustive list of specific examples of computers includes the following: Dell ALIENWARE™ desktops, Lenovo THINKPAD® laptops, SAMSUNG™ handsets, Google ANDROID™ smartphones, Apple IPAD® tablets, IBM BLADECENTER® blade servers, PEBBLE™ wearable computer watches, Google GLASS™ wearable computer glasses, or any other device having one or more processors and one or more storage devices, and capable of functioning as described in this application.

A processor may be any device that accepts data as input, processes it according to instructions stored in a storage component, and provide results as output. A person of ordinary skill in the art will recognize the variety of types of processors suitable for the functions disclosed, including general purpose processing units and special purpose processing units. A non-exhaustive list of specific examples of processors includes the following: Qualcomm SNAPDRAGON™ processors; Nvidia TEGRA® 4 processors; Intel CORE™ i3, i5, i7 and i8 processors; TEXAS INSTRUMENTS™ OMAP4430; ARM® Cortex-M3; and AMD OPTERON™ 6300, 4300, and 3300 Series processors. Each computer may have a single processor or multiple processors operatively connected together (e.g. in the "cloud").

A storage device is any type of non-transitory computer readable storage medium. A person of ordinary skill in the art will recognize the variety of types of storage devices suitable for the functions disclosed, including any electronic, magnetic, optical, electromagnetic, infrared, or semiconductor system or device, so long as it does not reduce to a transitory or propagating signal. A non-exhaustive list of specific examples of storage devices includes the following: portable computer diskettes, hard disks, random access memory, read-only memory, erasable programmable read-only memory, flash memory, optical fibers, portable compact disc read-only memory (CD-ROM), optical storage devices, magnetic storage devices and magneto-optical storage devices. Each computer may have a single storage device or multiple storage devices operatively connected together (e.g. in the "cloud").

This disclosure may be implemented on one or more computers running one or more instances of a virtual machine. A virtual machine is a software implementation of a computer that executes programs like a physical machine. Thus, a single physical machine may function conventionally as a physical computer, while also implementing a virtual machine that can perform the same processes as the physical computer. Multiple instances of a virtual machine may run on one computer or across multiple computers. A person of ordinary skill in the art will recognize the variety of types of virtual machines suitable for the functions disclosed, including system level virtual machines, process level virtual machines, fictive computers, and distributed computers. A non-exhaustive list of specific examples of virtual machines includes the following: VMWARE® virtual machines and Oracle VM VIRTUALBOX™ virtual machines.

Embodiments of this disclosure that employ virtual machines may contain a hypervisor, which is also known as a virtual machine monitor. A hypervisor is a piece of computer software that creates, runs, and manages virtual machines. More than one virtual machine may be run by a single hypervisor. The hypervisor controls the utilization of one or more processors by one or more virtual machines and the utilization of one or more storage devices by one or more virtual machines. A person of ordinary skill in the art will recognized the variety of types of hypervisors suitable for the functions disclosed, including type one or "native" hypervisors, and type two or "hosted" hypervisors. A non-exhaustive list of specific examples of hypervisors includes: Oracle VMWARE® Server for SPARC, Oracle VM SERVER™ for x86, Citrix XENSERVER™, and VMWARE® ESX/ESXi.

For the purposes of this application, the term "computing component" means a computer, a virtual machine, or multiple computers or virtual machines functioning as a single component. The term "computer" is limited to physical machines. Generally, a computer functions as a computing component by implementing an operating system through which program code, which implements the methods of this system, is executed. When a virtual machine functions as a computing component, a computer implements a hypervisor which implements a separate operating system, through which the program code is executed.

As referenced above, a single computer may implement multiple computing components, wherein the computer itself functions as a computing component and concurrently implements one or more instances of a virtual machine. Each virtual machine functions as a separate computing component. Similarly, a plurality of computing components may be made up of separate computers, none of which implement a virtual machine, or a plurality of computing components may be implemented on a single computer wherein only the virtual machines function as computing components. Additional combinations are contemplated as well, such as where a computing component is implemented across multiple computers. For example, a hypervisor of a virtual machine may manage the processors and storage devices of three computers to implement a virtual machine that functions as a single computing component. A person of ordinary skill in the art will recognize the range of combinations of computers and virtual machines that are suitable for the functions disclosed.

Computing components may be operatively connected to one another or other devices, such as by a communications network. One skilled in the art will recognize the appropriate media over which multiple computing components may be operatively connected to each other in a manner suitable for the functions disclosed, including as a communications network that allows the computing components to exchange data such that a process in one computing component is able to exchange information with a process in another computing component. A non-exhaustive list of specific examples of transmission media includes: serial or parallel bus systems, wireless, wireline, twisted pair, coaxial cable, optical fiber cable, radio frequency, microwave transmission, or any other suitable electromagnetic transmission media.

As illustrated in FIG. 4, a brainwave collection device is shown as 400. Element 410 represents a computer having an electrode input and a brainwave response output. Attached to the brainwave electrode input is a structure having a plurality of electrodes configured to attach to the head of an individual of a group being tested. Attached to the brainwave response outlet is a brainwave database 430 where data relating to a comparison between stimuli and brainwave responses are stored; as shown as element 440.

Figure 5:
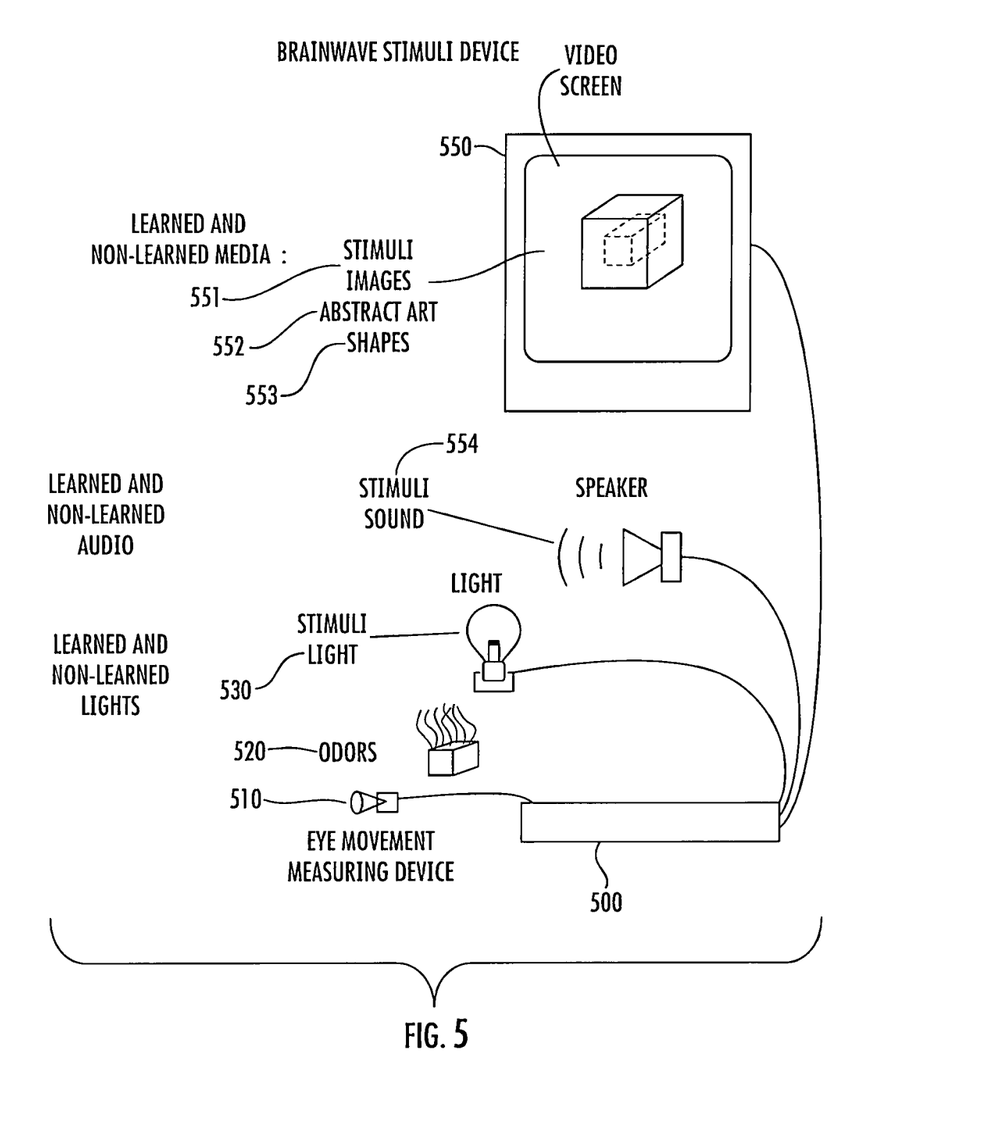
FIG. 5 illustrates a brainwave stimulation device.

FIG. 5 illustrates a brainwave stimuli device. The brainwave stimuli device includes a video screen 550 which displays images or sound to an individual being exposed to test stimuli. The stimuli may include images 551, abstract art 552 and shapes 553. Stimuli 540 represents sound as test stimuli. Further test stimuli can be odors 520 or eye movement 510, provided by eye measuring device 500. In addition, the stimuli can relate to learned and non-learned topics but most preferable is non-learned topics because if the individual has seen the stimuli in the past, it can alter their brainwave response to the stimulation. The stimuli may be provided in amounts of 5000 different stimuli shown at rates of 4-20 frames per second. At this speed, an individual's eyes may not be able to see or recognize the stimuli that will be recognized by the individual's brain, which is one reason why the invention is much more accurate than what was done in the past.

Figure 6:
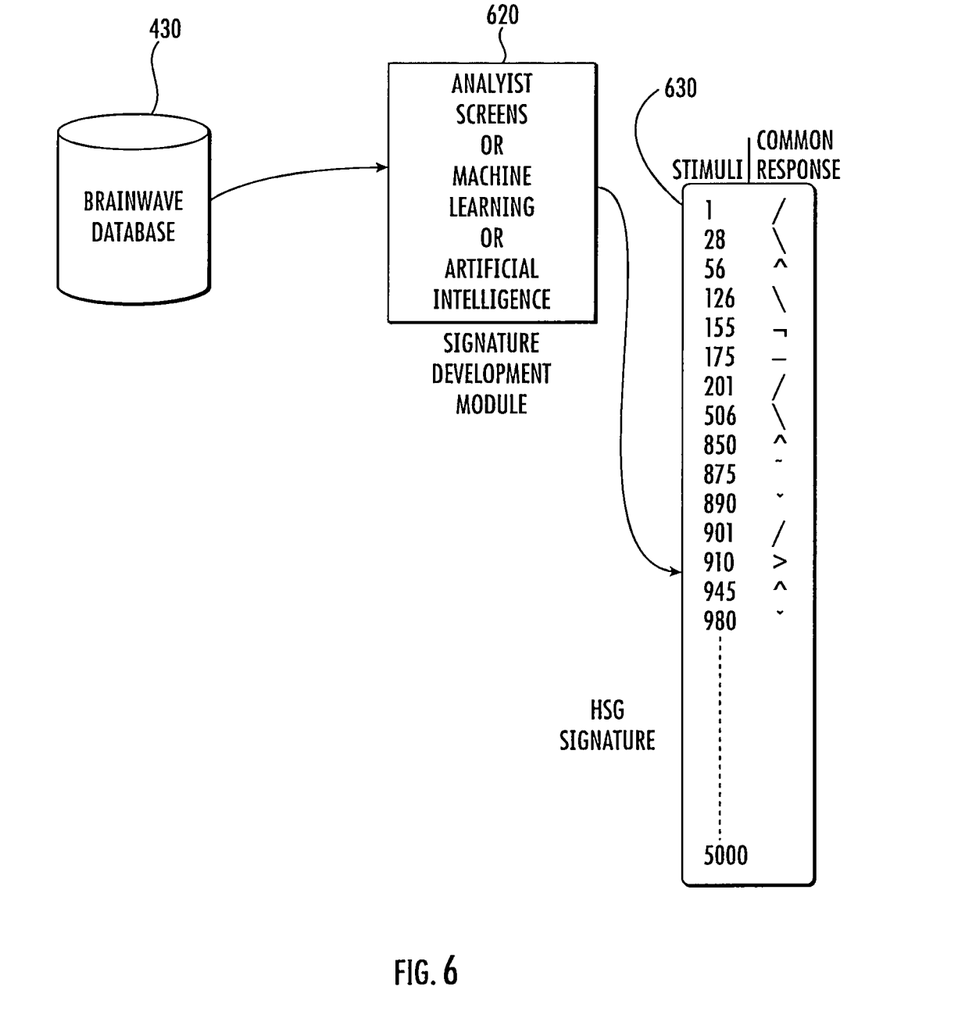
FIG. 6 illustrates a brainwave processing and analyzing device.

FIG. 6 illustrates a signature development module 620 which receives the stored brainwave responses from the brainwave database 430, and applies analyst screens or machine learning or artificial intelligence. Machine learning is an artificial intelligence technology that provides systems with the ability to learn without being explicitly programmed. There are numerous software systems based on Artificial Intelligence (AI) that will ingest massive amounts of data and look for patterns. Current face matching technology uses this proven approach buy ingesting hundreds of millions of photos with information as to which photos are the same person then the computer determining a very small data requirement for face matching. In this case, the computer would be requested to look for a pattern among the given HSG for each stimuli test. For example, there may be 5,000 stimuli tests and the AI model would look at how the group responded to each stimulus. If the group responded the same to the same stimuli, this point is a candidate for being part of the HSG signature. The belief is that out of 5,000 stimuli, only 300 or 500 would constitute the signature. As shown by element 630 is a representation of data comparing stimuli with brainwave responses.

Figure 7:
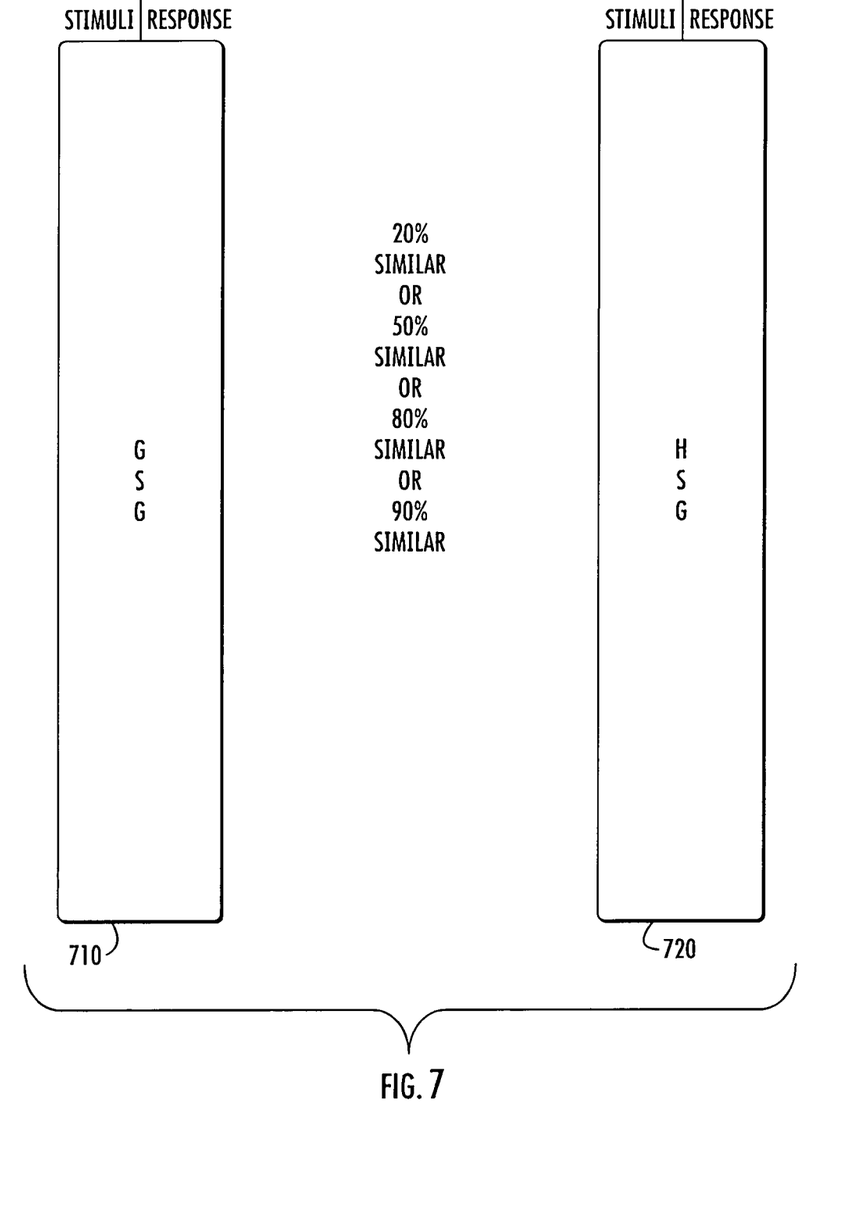
FIG. 7 illustrates different similarities between stimuli and responses between brainwaves of individuals of different groups.

FIG. 7 illustrates two sets of data 710 and 720 which compare the test stimuli and brainwave response between a highly skilled group and a general skilled group.

In FIG. 7, the HSG signature of 300 to 500 common response would be compared to a candidate from the General Skilled Group (GSG). The GSG individual would take the same or similar test to see the percent match the GSG has with the "gifted" HSG.

Over time, more Highly Skilled Groups would be added with their own signatures. This could then lead to testing a general population such as seniors in high school and determining whether the student has a "gift" by comparing their brainwave response to that of the HSG signatures.

This approach may be a better way to find which area a person has a gift rather than taking a Standard Aptitude Test (SAT). Game changing is being told your brainwave response is associated with this Highly Skilled Group and you may want to explore this area.

The above components are described in greater detail with reference to the figures. The descriptions set forth the various processes, relationships, and physical components of various exemplary embodiments of the subject matter of this disclosure.

Although exemplary embodiments have been shown, other exemplary embodiments would be understood by one of ordinary skill in the art. The invention is not limited in any way by the exemplary embodiments, but rather by the scope of the accompanying claims.

I claim:

1. A group association method comprising:
    selecting highly skilled individuals from a highly skilled group of individuals;
    selecting a plurality of test stimuli to be presented to each of the selected highly skilled individuals;
    presenting the plurality of test stimuli to each of the selected highly skilled individuals and collecting highly skilled brainwave responses via a plurality of electrodes corresponding to each of the plurality of test stimuli presented to each of the highly skilled individuals;
    analyzing the collected highly skilled brainwave responses for at least one of an amplitude value, a power value or a frequency value to identify a highly skilled brainwave response pattern for each of the highly skilled brainwave responses individuals, by comparing the at least one of the amplitude value, the power value or the frequency value between one of
        different regions of a plurality of electrode sensor regions of the plurality of electrodes, or
        electrode-pair channels of the plurality of electrodes;
    developing at least one brainwave response signature from a plurality of similar identified highly skilled brainwave response patterns;
    selecting general skilled individuals from a general skilled group of individuals;
    presenting the plurality of test stimuli to each of the selected general skilled individuals and collecting general skilled brainwave responses corresponding to each of the plurality of test stimuli presented to each of the general skilled individuals;
    analyzing the general skilled brainwave responses to identify at least one general skilled brainwave response pattern corresponding to at least one individual of the general skilled individuals;
    comparing the general skilled brainwave pattern to the at least one brainwave response signature from the plurality of similar highly skilled brainwave response patterns;
    identifying an individual from the selected general skilled individuals that have a high correlation of an identified general skilled brainwave pattern with the at least one brainwave response signature; and
    providing an indication of the identified individual from the selected general skilled individuals.

2. The group association method of claim 1, wherein the plurality of test stimuli include at least some test stimuli of the plurality of test stimuli being non-learned stimuli presented to the individuals.

3. The group association method of claim 1, wherein the plurality of test stimuli include test stimuli of the plurality of test stimuli being both learned and non-learned stimuli presented to the individuals.

4. The group association method of claim 1, wherein the plurality of test stimuli include test stimuli of the plurality of test stimuli being non-learned stimuli presented to the individuals.

* * * * *